(12) United States Patent
Trubetskoy et al.

(10) Patent No.: US 6,551,790 B2
(45) Date of Patent: Apr. 22, 2003

(54) PROCESS FOR GLUCURONIDATION SCREENING

(75) Inventors: Olga Trubetskoy, Middleton, WI (US); Robert G. Lowery, Brooklyn, WI (US)

(73) Assignee: PanVera LLC, Madison, WI (US)

( * ) Notice: Subject to any disclaimer, the term of this patent is extended or adjusted under 35 U.S.C. 154(b) by 0 days.

(21) Appl. No.: 09/455,202

(22) Filed: Dec. 6, 1999

(65) Prior Publication Data

US 2002/0076740 A1 Jun. 20, 2002

Related U.S. Application Data

(60) Provisional application No. 60/111,217, filed on Dec. 7, 1998.

(51) Int. Cl.[7] .............................. C12Q 1/48; C12Q 1/34; G01N 33/53
(52) U.S. Cl. .............................. 435/15; 435/18; 435/968
(58) Field of Search .............................. 435/15, 18, 968

(56) References Cited

U.S. PATENT DOCUMENTS

| 5,744,355 A | * | 4/1998 | Weinshilboum et al. ..... 435/325 |
| 6,080,551 A | * | 6/2000 | Doyle et al. ................. 435/7.4 |
| 6,096,531 A | * | 8/2000 | Rutkowski ............... 435/262.5 |

OTHER PUBLICATIONS

Glatt et al, Molecular Toxicology, vol. 1(4), p313–334, (1987–1988) (Abstract Only).*

* cited by examiner

Primary Examiner—Louise N. Leary
(74) Attorney, Agent, or Firm—PanVera LLC; Andrew S. Marks

(57) ABSTRACT

A fluorescence polarization process used to identify activity of conjugative enzymes involved in xenobiotic transformations, such as glucuronosyltransferases is provided.

8 Claims, 3 Drawing Sheets

PROCESS FOR GLUCURONIDATION SCREENING

CROSS-REFERENCE TO RELATED APPLICATIONS

This application claims the benefit of U.S. provisional application Serial No. 60/111,217, filed Dec. 7, 1998.

FIELD

The geld of this invention relates to a process for screening for enzymes activity. More particularly the process is a method that can be used to identify activity of glucuronosyltransferases.

BACKGROUND

Drub metabolism problems such as production of toxic metabolites and unfavorable pharmacokinetics cause almost half of all drug candidate failures during clinical trials. Although glucuronidation is one of the most important routes of biotansformation, the broad and overlapping substrate specificity of the hepatic uridine diphosphate glucuronosyltransferases UDP-glucuronosyltransferases (UGTs) that catalyze glucuronidation remains poorly understood. The two main reasons for this situation are the lack of isolated individual UGT isozymes and the lack of assay methods suitable for detecting glucuronidation of diverse chemicals.

The UDP-glucuronosyltransferases are a family of enzymes that catalyze the glucuronidation of endogenous and xenobiotic chemicals (Equation 1), generating products that are more hydrophilic and thus more readily excreted in bile or urine.

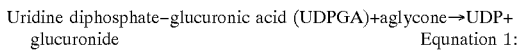

Uridine diphosphate–glucuronic acid (UDPGA)+aglycone→UDP+ glucuronide     Equnation 1:

The UGTs play a key role in several important metabolic functions, including:

- elimination of drugs such as non-steroidal anti-inflammatories, opioids, antihistamines, antipsychotics and antidepressants,
- detoxification of environmental contaminants such as benzo(a)pyrenes,
- regulation of hormone levels for androgens, estrogens, progestins, and retinoids,
- elimination of the heme degradation product bilirubin.

Although glucuronidation generally is classified as Phase II metabolism—the phase occurring after P450 dependent oxidative metabolism—many compounds do not require prior oxidation because they already possess functional groups that can be glucuronidated. Examples of first pass metabolism catalyzed by UGTs include the UGT2B7-dependent glucuronidation of morphine and the glucuronidation of 5-lipoxygenase inhibitors (anti-inflammatories). In the latter case glucuronidation was demonstrated to be the rate-limiting step for in vivo plasma clearance.

Notably, glucuronidation does not always cause decreased biological activity and/or deoxification. Glucuronides of some drugs are toxic, and have been linked with adverse drug reactions including immune hypersensitivity. Glucuronidation can modulate the potency of some drugs: the 6-glucuronide of morphine is a more potent analgesic than the parent compound, whereas the 3-glucuronide is a morphine antagonist. In addition, steroid glucuronidation can produce more active or toxic metabolites under pathophysiological conditions or during steroid therapies.

UGTs are 50–60 kDa integral membrane proteins with the major portion of the protein, including the catalytic domain, located in the lumen of the endoplasmic reticulum and a C-terminal anchoring region spanning the ER membrane. Two UGT families—UGT1 and UGT2—have been identified in humans. Although the members of these families are less than 50% identical in primary amino acid sequence, they exhibit significant overlap in substrate specificity.

The members of the UGT1 family that are expressed in human liver, where the majority of xenobiotic metabolism takes place, include UGT 1 A1, 1A3, 1A4, 1A6, and 1A9. Although the UGT2 family has not been studied as extensively, it is known that UGT2B4, 2B7, 2B10, 2B15 and 2B17 are expressed in the liver. Mutations in UGTs are known to have deleterious effects, including hyperbilirubinemia which occurs with a frequency of 5–12% and can lead to neurotoxicity and in severe cases, death. As is the case for other drug metabolizing enzymes such as P450s, interindividual differences in UGT expression levels have been observed and linked to differences in drug responses. For instance, low expression of UGT1A1, as in patients with Gilbert's syndrome, has been associated with the toxicity of Irinotecan, a promising anticancer agent. In addition, UGT upregulation in tumor tissues has been identified as a possible cause of anticancer drug resistance.

Specificity for Aglycones. UGT substrates are known as aglycones. The products of the reaction are called glucuronides. All of the known UGTs exhibit broad substrate specificity, with a single isozyme catalyzing glucuronidation of a broad range of structurally unrelated compounds. Not surprisingly there also is a great deal of overlap in the specificities of UGT isozymes. The sites of glucuronidation generally are nucleophilic nitrogen, sulfur or oxygen atoms in functional groups such as aliphatic alcohols, phenols, carboxylic acids, primary through tertiary amines, and free sulfyhydryls. The aglycone binding site is believed to be in the N-terinal portion of the UGT polypeptide, the region of the protein that shows the greatest variability in sequence among isozymes. However, efforts to define the aglycone binding site by correlating N-terminal amino acid sequences of UGT isozymes with their substrate specificities have been unsuccessful.

Despite their broad substrate specificities, UGTs can be highly regio- and stereo-selective. It has been suggested that substrates bind loosely to a very "open" substrate binding pocket—as with some P450s—and rotate until reactive functional groups are suitably oriented to the bound UDPGA and the amino acids involved in catalysis. Although several studies on the substrate specificities of individual recombinant UGTs have been performed, most have been limited to a relatively small number of compounds within one or two structural classes.

HTS assay methods described herein can be used to rapidly screen large numbers of diverse chemicals thus allowing a systematic effort to fully define the "chemical space" recognized by each of the key hepatic UGTs. Moreover, these HTS assay methods will fulfill the immediate needs of the pharmaceutical industry by providing a means to screen large numbers of diverse compounds for glueuronidation with a panel of the key human UGT isozymes. The information obtained with these HTS assays can be used in the following ways:

After isozyme identification, more detailed kinetic studies with the appropriate UGT isozyme can be used to predict in vivo clearance rates, reducing the number of compounds that fail in clinical studies due to poor pharmacokinetics.

Knowledge of metabolism by a specific UGT alerts the drug discovery team to potential pharmacogenetic problems, since genetic differences in UGT levels are recognized as an important factor in varying responses to therapeutics.

Identification of the UGT responsible for the metabolism of a drug will aid in judicious selection of the in vitro assays or animal models used for preclinical assessment of possible drug-drug interactions and toxicology testing, thereby reducing inappropriate or unnecessary use of animals for experiments.

Metabolism data can be used as a component of rational drug design. A better understanding of the structure-activity relationships that define substrate specificity for the various UGT isozymes would provide a basis for structural modifications of primary compounds to change their metabolism profile. This approach was used successfully for development of ABT-761, a 5-lipoxygenase inhibitor.

The testing of glucuronidated compounds can lead to the discovery of valuable podrus that are inactive until metabolized in the body into an active form.

To confirm the need for improved technology to probe the specificity of UGT isozymes, it is useful to review the methods currently employed for in vitro drug metabolism studies, and the reasons why they are not adequate for immediate drug discovery needs.

Sources of UGTs. The important drug metabolizing UGT isozymes are located in the endoplasmic reticulum of liver cells. Natural sources of UGT for in vitro assays include liver slices, cultured cells, and cell fractions such as human liver microsomes. The major drawbacks of these unpurified systems are that they contain a mixture of multiple UGT isozymes and other drug metabolizing enzymes. As a result, they are of limited use in obtaining meaningful data on a specific UGT isozyme—particularly in an HTS format. Heterologous expression systems such as mammalian and BaV-infected insect cells have made it possible to produce large amounts of microsomal membranes highly enriched in a single UGT isozyme.

Assay methods. UGTs generally are assayed by isolation and quantification of the radioactively labeled metabolites produced from the parent compound in reactions containing radiolabeled UDPGA. In most cases, this involves chromatographic techniques such as thin layer chromatography (TLC) or high pressure liquid chromatography (HPLC), and in some cases phase separations. There are two major drawbacks to these assays methods. First, the need to isolate the reaction products makes the methods too cumbersome and time consuming for use in any type of high volume assay format. Second, different glucuronidated metabolites have different chromatographic properties, raising an obvious technical barrier to screening diverse compounds for metabolism by a panel of isolated UGT isozymes. For some substrates, products and reactants can be differentiated on the basis of altered absorbance or fluorescence after glucuronidation. However, these methods are limited to a few UGT isozymes.

SUMMARY

The present invention provides a universal HTS activity assay that enables screening for glucuronidation of large numbers of diverse chemicals by any isolated recombinant UGT using a single detection method. The method is based upon glucuronides, the products of UGT reactions, inhibiting the formation of a fluorescent product by a bacterial $\beta$-glucuronidase. The method is non-radioactive, homogenous and can be used for identification of novel UGT substrates and inhibitors in a high throughput screening (HTS) format. UGT assay methods provided herein are based on inhibition of a fluorescent $\beta$-glucuronidase reporter reaction. This approach provides the following advantages over existing methods:

Universal Assay Method. The assay method is useful for all UGT isozymes and for all aglycone substrates, thus making it ideal for screening large numbers of diverse compounds.

Nonradioactive. The assay does not employ radioisotopes, thus eliminating the hazards and regulatory and handling costs associated with such agents.

Homogeneous Assay Method. The assay is homogenous, eliminating separation steps and possibly allowing continuous monitoring of reaction rate, in turn allowing more flexibility for kinetic analyses.

The novel HTS assay method will allow investigators to survey the full range of potential substrate specificity for the key hepatic UGT isozymes.

Assay Principle: Cleavage of 4-methylumbelliferyl $\beta$-D-glucuronide by bacterial $\beta$-glucuronidase generates the highly fluorescent compound, 4-methylurnbelliferone. Diverse $\beta$-D-glucuronides act as competitors of $\beta$-glucuronidase, thus providing the basis of a coupled assay method for detection of glucuronide production by recombinant UGT isozymes. Using human recombinant human UGT 1A6 as an example, the present invention demonstrates the feasibility of using this coupled assay method for fluorescence detection of UGT activity with several structurally diverse substrates. The 4-methylumbelliferyl β-D-glucuronide cleavage assay can easily be adapted to high throughput formats to detect the presence of β-D glucuronides generated using recombinant glycosyl transferase preparations.

Methods

β-D-glucuronidase (Part G-7396), α-naphthyl β-D-glucuronide, β-trifluoromethylumbelliferyl β-D-glucuronide, β-estradiol 3-(β-D-glucuronide), p-acetominophenyl β-D-glucuronide, 5β-androstane-3α, 17α-diol-11-one-17-carboxilic acid- 3-(β-D-glucuronide), UDPGA and 4-methylumbelliferyl β-D-glucuronide were obtained from Sigma, St. Louis Mo. Tetrahydrocortisone 3-β-D-glucuronide was obtained from Molecular Probes, Eugene, Oreg. Recombinant control and UGT1A6 membrane preparations were generated and are commercially available from PanVera Corporation, Madison Wis. All other reagents were analytical grade or better and purchased from a variety of commercial sources.

Results and Discussion

Figure 1A:
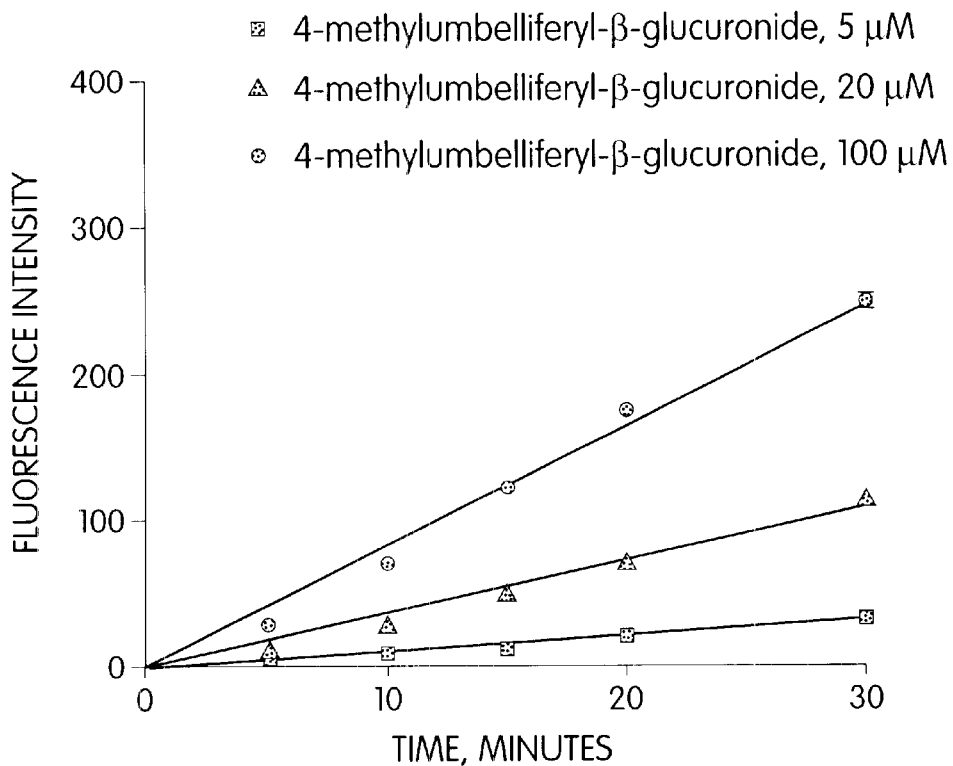
FIG. 1, panel A, depicts the kinetics of the cleavage of various concentrations of 4-methylumbelliferyl-$\beta$-D-glucoronide by $\beta$-glucuronidase, as measured by fluorescence intensity. Panel B depicts the velocity of cleavage of various concentrations of 4-methylumbelliferyl-$\beta$-D-glucoronide by $\beta$-glucuronidase.
Figure 1B:
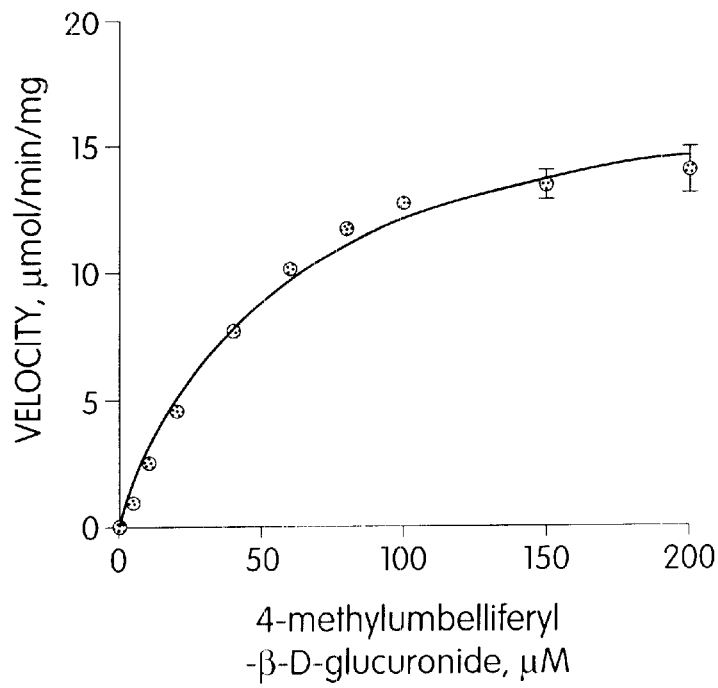

An assay that can be used to demonstrate the presence of β-D-glucuronides that might be generated from different classes of UGT enzymes is provided. An assay based on β-glucuronidase activity provides a high throughput screening method to identify structurally different β-D-glucuronides. Cleavage of 4-methylumbelliferyl β-D-glucuronide yielded the highly fluorescent compound 4-methylumbelliferone. Under liner conditions of protein concentration and incubation time, the apparent $K_m$ value for cleavage of 4-methylumbelliferyl-β-D-glucuronide was approximately 56 µM (FIG. 1, panels A and B).

Figure 2:
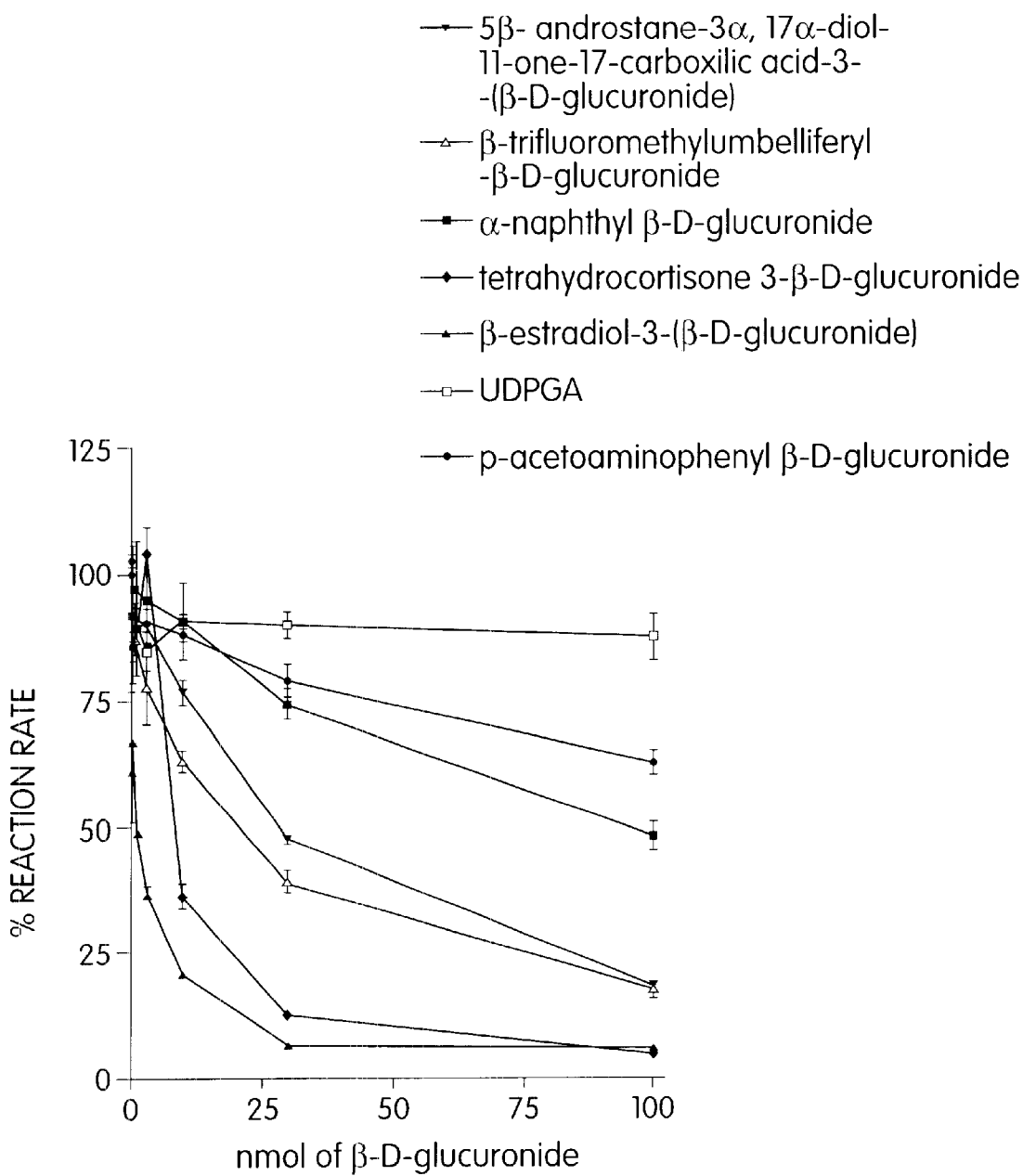
FIG. 2 depicts the effect of varying concentrations of $\beta$-D-glucuronide on the ability of $\beta$-glucuronidase to cleave various substrates.

In order to show the feasibility of developing a high throughput inhibition assay, we examined the potential of a variety of structurally dissimilar, commercially available β-D-glucuronides to act as inhibitors for the cleavage of 4-methylumbelliferyl-β-D-glucuronide. These β-D-glucuronides represent compounds that might potentially be formed by UGT activity e.g. phenol and steroid glucuronides. FIG. 2 shows that all of the β-glucuronides tested inhibited the production of 4-methylumbelliferone by β-glucuronidase. The potential to inhibit 4-methylumbelliferyl-β-D-glucuronide cleavage appeared to be dependent on the chemical nature of the substituted aglycone, with β-estradiol-3-(β-D-glucuronide) and α-naphthyl β-D-glucuronide showing the strongest and weakest inhibition, respectively. Uridine 5'-diphosphoglucuronic acid (UDPGA), an essential cofactor for UGTs was not an effective competitor over the range tested, probably due to the α configuration of sugar bond to UDP (Parkinson, 1996).

Figure 3A:
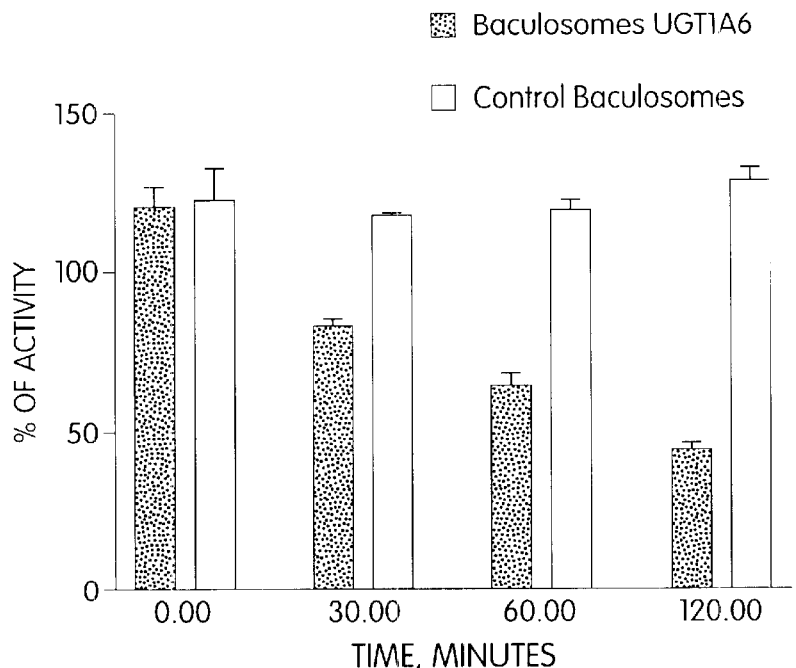
FIG. 3, panel A, depicts the results of an experiment wherein a microsomal preparation from either recombinant insect cells engineered to express the UDP glycosyl transferase UGT1A6 ("Baculosomes UGT1A6") or non-recombinant insect cells ("Control Baculosomes") is incubated with $\alpha$-naphthol for various periods of time and any resulting $\alpha$-naphthyl glucuronide is extracted and added to a mixture of 4-methylumbelliferyl-$\beta$-D-glucoronide and $\beta$-glucuronidase. The effect of such an extrit on the ability of $\beta$-glucuronidase to cleave 4-methylumbelliferyl-$\beta$-D-glucoronide as compared to reaction lacking such extract is shown ("% of activity"). Panel B depicts the results of an experiment wherein a microsomal preparation from either recombinant insect cells engineered to express the UDP glycosyl transferase UGT1A6 ("Baculosomes UGT1A6") or non-recombinant insect cells ("Control Baculosomes") is incubated with or without $\alpha$-naphthol for various periods of time and then directly added (without extraction) to a mixture of 4-methylumbelliferyl-$\beta$-D-glucoronide and $\beta$-glucuronidase. The effect of the baculosomes on the ability of $\beta$-glucuronidase to cleave 4-methylumbelliferyl-$\beta$-D-glucoronide as compared to reacion without baculosomes is shown ("% of activity").
Figure 3B:
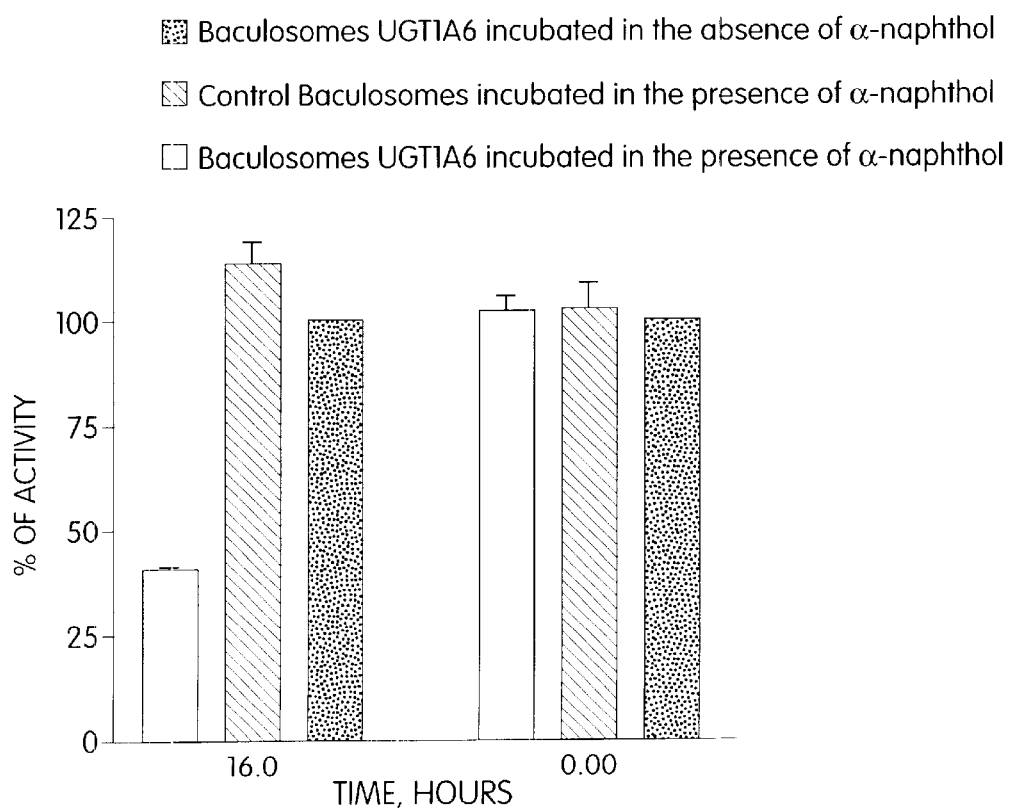

Two approaches were taken to test the feasibility of coupling the UGT-dependent production of glucuronides to inhibition of fluorescent product formation by β-D-glucuronidase. The first involved extracting the UGT reaction products and adding them to the β-D-glucuronidase fluorescence assay reagents. The second involved adding the β-D-glucuronidase reaction components directly to the quenched UGT reaction. In the first approah, α-naphthyl β-D-glucuronide was generated in with a reaction involving recombinant human UGT1A6 and α-naphthol. Following extraction, 4-methylumbelliferyl-β-D-glucuronide assay reagents were added to the extracted, dried reaction residues. In a separate experiment it was shown that aglycones as well as glucuonides are extracted with ethyl acetate and hence transferred to the β-glucuronidase reporter assay. FIG. 3, panel A, shows that residues from the UGT1A6 assay, but not the control microsome assay, inhibited 4-methylumbelliferyl-β-D-glucuronide cleavage. Residues from the 0 time point extractions do not appear to inhibit the 4-methylumbelliferone cleavage assay which indicated that the aglycone (β-naphthol does not interfere non-specifically with this assay under these conditions. Inhibition of 4-methylumbelliferyl-β-D-glucuronide cleavage was dependent on the incubation time of the UGT1A6 assay, presumably reflecting increased α-naphthyl glucuronide accumulation. (Accumulation of β-naphthyl glucuronide in the UGT1A6 assay was independently verified in a parallel experiment using [$^{14}$C] UDPGA, data not shown.)

In the second approach, 4-methylumbelliferyl-β-D-glucuronide assay reagents were added directly to a β-naphthyl glucuronidation assay that was performed in a 96 well plate. FIG. 3, panel B, shows that 4-methylumbelliferyl β-D-glucuronide cleavage was 60 percent slower when added to the UGT1A6 assay compared to the control. The horogeneous format circumvented the need for extraction, but required longer incubation periods with the recombinant enzyme. These results demonstrate that: i) the 4-methylumbelliferyl-β-D-glucuronide assay can be used to detect β-D-glucuronides generated in biological preparations, ii) the choice of α-naphthol β-D-glucuronide, which is a weak competitive inhibitor (FIG. 2) adds credence to this assay. More potent inhibitors such as estradiol β-D-glucuronide (FIG. 2) are likely to be more effective, iii) the assay is amenable to a high throughput format, as a two step procedure, and iv) heterologous expression systems are useful for the generation of high concentrations of β-D-glucuronides, such as α-naphthyl β-D-glucuronide, which was a weak competitor in the β-D-glucuronide cleavage assay (FIG. 2).

In summary, we have demonstrated the feasibility of using a fluorescent assay that can be adapted to a high throughput format to measure the presence of β-D-glucuronides. The assay described here uses relatively inexpensive reagents and does not require chrormatographic resolution (TLC or HPLC) or radioactivity. The assay can be performed in a homogeneous format and could be easily automated. The assay will not eliminate the usefulness of other analytical procedures needed to determine the kinetic parameters of glucuronidation, but shows potential as a rapid preliminary screening method.

In addition, similar principles and procedures described here for UDP-glycosyltransferases could be applied to other important classes of phase II conjugating enzymes, e.g. sulfotransferases, N-acetyltransferases, glutathione S-transferases. For example, sulfation catalyzed by members of the sulfotransferase enzyme family is a major metabolic pathway which modulates the biological activity of numerous endogenous and xenobiotic chemicals. Sulfate conjugates from sulfation assays would be expected to compete in a similarly designed assay that used a sulfatase to generate a fluorescent product. The following procedure can be used to demonstrate the presence of sulfated compounds generated from multiple sources of sulfotransferases including recombinant enzymes, tissue homogenates and biological fluids. Aryl-sulfatase enzyme, which is capable of cleaving a wide variety of sulfated compounds, can be used to design a high-throughput fluorescent assay where the products of sulfotransferase conjugation would act as competitive substrates for aryl-sulfatase cleavage of the reporter fluorescent or chromogenic substrate. The sulfatases belong to a highly conserved gene family. Considerable sequence similarity exists among sulfatases of both prokaryotic and eukaryotic origins. Sulfatases of prokaryotic origin are preferable to use because of their wiser substrate specificity (for example, sulfatase type IV–VIII; H1-H5 from Sigma). Possible substrates for assaying aryl-sulfatase activity include the fluorogenic ELF-97 sulfatase substrate (ELF-97 sulfate, E-6579, Molecular Probes) and the chromogenic indolyl substrates (B-8406, B-8410, Molecular Probes). ELF-97 sulfate is expected to yield alphotostable yellow-green fluorescent precipitate, whereas the indolyl sulfates (B-8406, B-8410) produce dark blue and magenta precipitates, respectively. The measurement of the cleavage of ELF-97 sulfate (Molecular Probes, OR) by sulfatase to the highly fluorescent compound will be possible using excitation wavelength of 345 nm and emission wavelength of 530 nm. Competitive inhibition of ELF-97 sulfatase cleavage will be used to detect the presence of sulfated metabolites of the test compound in the sulfotransferase reaction assay mixture.

Production of purified, full length UGT2B7 from BaV infected insect cells. To establsh a model for ultimate development of QSAR methods for all key UGTs, UGT2B7 is purified from BaV-infected insect cells for incorporation into the HTS assay method. Although there are no published reports on purification of UGTs from BaV-infected insect cells, we will employ methods used successfully to purify various UGT isozymes from native sources and to maintain their stability with lipids. We and other investigators already have demonstrated that the properties of the BaV-expressed UGTs are similar to those of the enzymes expressed in mammalian cells. Use of the BaV expression system as a source for the purified enzyme will allow cost effective production of sufficient protein for use of the proposed HTS assay in pharmaceutical drug discovery programs and for the planned QSAR studies.

Production of a soluble aglycone binding domain for structural studies. Structural studies on UGT/aglycone complexes will aid in the development and validation of QSAR models. NMR analysis combined with molecular docking simulations is used to determine the bioactive conformations of substrates and to identify molecular interactions involved in binding and subsequent glucuronidation. Experiments with UGTs containing mutations in proposed active site residues are used to test the structural models. These structural studies will provide a powerful approach that is synergistic with HTS screening for identification of the key molecular recognition factors that affect UGTs catalysis. To circumvent the difficulties inherent in structural studies with membrane proteins, an affinity-tagged soluble UGT2B7 aglycone binding domain in E. coli will be produced and purified. This approach provides the following advantages: a) elimination of the need for lipids to maintain structural integrity due to removal of the C-terminal portion of the protein that interacts with the membrane, b) high level expression of a soluble domain in the optimal size range for NMR studies, and c) affinity tagging of binding domains, thus simplifying purification.

The HTS assay is used to identify and determine the kinetic parameters for diverse UGT substrates used in the QSAR study. QSAR is a rational design tool that has been used for more than 30 years by medicinal chemists to improve the potency and metabolism properties of drugs, and to assess chemical toxicity. The concept is based on the ability to quantitatively relate changes in the bioactivity of small molecules to changes in their physical properties. In a typical QSAR study, a defined set of chemicals—the training set—is tested for interaction with a protein of interest, usually receptor binding or enzymatic conversion. Correlations are then sought between the physicochemical properties of the chemicals and their bioactivity. A primary goal of QSAR is to predict the potency of chemicals outside of the training set. In a medicinal chemistry setting, QSAR analysis typically is performed using a high affinity receptor and a training set of 10–50 compounds in a single congeneric series—a group of chemicals sharing a common molecular core with relatively minor substituent or structural variations on that core. Such an approach is not applicable to the UGTs because a single isozyme may have very broad substrate specificity, encompassing several structural classes.

To effectively address the structural diversity of UGT substrates, UGT QSAR that will focus on the catalytic mechanism (i.e., how the physicochemical properties of UGT substrates affect their binding to UGT and subsequent nucleophilic attack on the UDPGA molecules) will be used. The key molecular recognition factors that determine aglycone binding and reactivity at the active site with the assumption that two structures can present similar recognition factors within dissimilar molecular frameworks will be identified. Establishing the QSAR based on the fundamental interactions that trigger catalysis should enable prediction of glucuronidation for molecules with diverse molecular frameworks. The assay methods developed are used to generate quantitative kinetic data ($V_{max}$ and $K_m$) using in vitro assays with purified recombinant enzyme, thereby allowing a mechanism based QSAR analysis of UGT catalysis and eliminating many of the extrinsic factors that might interfere with the analysis using less refined systems.

The success of QSAR in these applications partially depends upon how effectively the structures in the training set probe the "chemical space" defined by the enzyme active site and the mechanism of its bioactivity. Although the high throughput assay methods developed will allow a "shotgun approach" by screening hundreds of thousands of compounds, such a collection of purified compounds would cost several million dollars. Instead, a smaller focused library of several thousand compounds that are likely to be glucuronidated will be designed. This is achieved using database searching tools with known glucuronidation reactions and chemical logic as inputs. The focused library then is screened using the HTS method described herein to identify those compounds metabolized by UGT2B7. This subset, an estimated 500–1500 compounds, will comprise the QSAR training set. Thus the HTS assay methods provided herein are used in both a qualitative screening mode to develop the UGT2B7 QSAR training set, and in an analytical mode for probing the molecular determinants of UGT catalysis.

Additional UGT isozymes are incorporated into the HTS activity assay. The invention also provides a second assay based on detection of UDP, a reaction product common to all UGT isozymes. When used in HTS format, this assay can be utilized with all of the key hepatic UGT isozymes. Four of the UGT1 family isozymes have been produced as microsomal membrane preparations from BaV-infected insect cells. These USTs and additional members of the UGT2 family are purified and incorporated into the universal UDP-based HTS assay, thereby providing the capability to screen compound libraries for UGT isozyme identification and pharmacokinetics with the full spectrum of hepatic glucuronidation activity.

The soluble aglycone binding domain provides structural information on bound aglycones. Structural analyses of bound aglycones and their interactions with active site amino acid residues enhance the QSAR by providing an independent approach for identifying the key molecular recognition factors that determine aglycone binding and reactivity. Three-dimensional models of the bound aglycones aid in the application of Powerful 3D-QSAR approaches, such as comparative molecular field analysis. Mapping of aglycone-UGT interactions aid in the application and validation of fragment based QSAR approaches such as Holographic QSAR (Tripos, St. Louis, Mo.) or Multicase (Mulicase, Inc. Beachwood, Ohio). In the end, it is important to note that QSAR is based on statistical correlations. The structural studies will provide a means of assessing whether these correlations are consistent with empirically determined steric and spatial constraints for substrate binding and catalysis.

Heterologous expression and characterization of full length UGT 2B7. It has recently demonstrated that stably expressed human UGT2B7 catalyzed the glucuronidation of opiolds such as morphine and buprenorphine with high efficiency (Dr. Thomas Tephly, University of Iowa College). In addition, UGT2B7 has been shown to catalyze the glucuronidation of NSAIDS and catechol estrogens. Dr. Tephly's studies with UGT 2B7 expressed in mammalian cells have clearly established the isozyme's importance in the metabolism of drugs and endogenous steroids, and will provide important benchmark data for evaluating the enzyme purified from BaV-infected insect cells during studies.

properties of the recombinant enzyme. Glucuronidation activity towards opioids (5 mM morphine (pH 8.4), 5 mM codeine (pH 7.7), 2 mM nalorphine (pH 8.4), 2 mM naloxone (pH 7.7), 2 mM naltrexone (pH 7.0) and 0.5 mM buprenorphine (pH 7.0)) was demonstrated using the method described by Puig and Tephly. These studies also indicated that UGT2B7 promotes the glucuronidation of the 3-OH and 6-OH of codeine with an efficiency ratio similar to the ratio of glucuronides found in human urine, or 7 to 1; 3-OH to 6-OH. In addition, codeine, the 3-methoxy derivative of morphine, was efficiently converted to the 6-O-glucuronide by UGT2B7.

Besides its important role in opioid and NSAID metabolism, UGT2B7 is polymorphic, having been cloned and expressed previously with a tyrosine (UGT2B7Y(268)) or a histidine (UGT2B7H(268) at amino acid 268. Questions have been raised concerning the substrate specificity or even the relative reactivity of the two enzyme forms with certain subsrates. UGT2B7Y(268) was reported to be active toward menthol and androsterone glucuronide formation by one laboratory, while another has reported that UGT2B7H(268) is inactive with these substrates. In addition, these investigators proposed that individual differences in the expression levels of the two UGT2B7 forms accounts for the variability in the ratio of (S)- to (R)-glucuronides of oxazepam detected in urine and plasma samples.

TABLE 1

Kinetics of glucuronidation with various opioid substrates using membrane preparations of HK293 cells stably expressing either UGT2B7Y(268) or UGT2B7H(268) using two different passages of cultured cells.

| | UGT2B7Y | | | UGT2B7H | | |
|---|---|---|---|---|---|---|
| Substrate | $K_m$ ($\mu M$) | $V_{max}$ pmol/min/mg protein | Efficiency $V_{max}/K_m$ (x100) | $K_m$ ($\mu M$) | $V_{max}$ pmol/min/mg protein | Efficiency $V_{max}/K_m$ (x100) |
| morphine, 3-glu | 458, 490 | 5050, 5900 | 1100, 1200 | 633, 331 | 4779, 3054 | 754, 922 |
| morphine, 6-glu | 432, 670 | 485, 749 | 112, 111 | 311, 236 | 413, 498 | 132, 211 |
| nalorphine | 77, 121 | 2870, 3650 | 3700, 3000 | 141, 171 | 3990, 4670 | 2850, 2700 |
| naloxone | 50, 40 | 3750, 2550 | 7500, 6300 | 41, 60 | 3810, 4530 | 9300, 7550 |
| naltrexone | 140, 180 | 840, 1130 | 600, 600 | 63, 200 | 1000, 1120 | 1600, 560 |
| hydromorphone | 410, 500 | 1450, 1770 | 350, 350 | 390, 360 | 1500, 1600 | 380, 450 |
| oxymorphone | 1360, 900 | 5640, 6040 | 400, 650 | 540, 670 | 7510, 8570 | 1385, 1285 |
| codeine | 230, 360 | 190, 40 | 83, 11 | 791, 550 | 97, 110 | 12, 20 |
| buprenorphine | 3, 1 | 580, 900 | 19400 | 22 ± 6 | 400 ± 40 | 1840 |
| S-propanolol | 184, 54 | 70, 140 | 38, 259 | 72 ± 19 | 148 ± 30 | 205 |
| R-propanolol | 180 | 96 | 53 | 101, 72 | 194, 86 | 192 |
| androsterone | 7.4, 6.1 | 372, 962 | 5027, 15874 | 7.2, 12.2 | 584, 909 | 8100, 7443 |

Clinical studies have shown that morphine-6-O-glucuronide is 2–3 times more effective as an analgesic than the parent compound and that it binds with high affinity to opioid receptors. In contrast, morphine-3-O-glucuronide does not bind to the opioid receptors and is devoid of analgesic effects. Furthermore, morphine-3-O-glucuronide has been shown to counteract the analgesic activity of morphine and morphine-6-O-glucuronide.

As a first step towards understanding the metabolism of morphine a UGT2B7, cDNA was isolated from a human liver library based on homology with the full length rat liver cDNA for UGT2B1, which has activity toward opioids. Stable UGT2B7 cell lines were established from embryonic human kidney cells (HK293 cells) and microsomal membrane fractions from these cells were used to assess the To confirm the roles of the two forms of UGT2B7 in the metabolism of drugs and endobiotics, studies on the glucuronidation of opioid compounds, agonists, partial agonists and opioid antagonists using stably expressed UGT2B7Y and H and optimized experimental conditions were performed (Dr. Telphy) (Table 1). This work also demonstrated the role of UGT2B7 in glucuronidation of certain androgenic steroids and xenobiotics including propranolol, and additional compounds not shown in Table I.

Development of HTS assay methods for UGTs.

TABLE 2

Detection of glucuronidation by coupling to the inhibition of a fluorescent β-glucuronidase reporter reaction.

| | |
|---|---|
| 1. UGT reaction: | UDPGA + Aglycone → UDP + Glucuronide |
| 2. β-glucuronidase reaction: | 4-methylumbelliferyl-β-D-glucuronide + H$_2$O 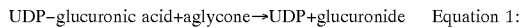 glucuronic acid + 4-methylumbelliferone* (360 nm Ex, 440 nm Em) |

The assay outlined in the above box is described in detail earlier in the application. Because this assay was developed for limited qualitative analysis only, it does not meet all of the requirements for the UGT QSAR proposed. However, it demonstrates the feasibility of using a simple non-radioactive assay in a high-throughput format to detect UGT activity. The assay principle is based on the ability of glucuronides produced in UGT reactions to competitively inhibit a fluorescence based β-glucuronidase reporter react on.

After identifying a suitable β-glucuronidase and determining the optimal concentrations of vious assay components, the fluorescent assay was tested for its ability to detect β-glucuronides generated by a recombinant UGT enzyme. Products from a UGT1A6 glucuronidation assay inhibited the methylumbelliferyl-β-D-glucuronide cleavage assay and the extent of inhibition was dependent on the incubation period for the UGT1A6 reaction. (The accumulation of β-naphthyl glucuronide in the UGT1A6 reaction was independently verified in a parallel experiment using UDP[$^{14}$C]-GA). To establish the feasibility of performing the assay in an HTS format, the assay was conducted in a 96 well plate in a homogenous format, i.e., without extracting the glucuronide produced in the UGT reaction prior to starting the β-glucuronidase reaction. Inhibition of the β-glucuronidase reaction was dependent on the presence of recombinant UGT1A6 and on the aglycone substrate β-naphthol. The ability of several diverse glucuronides to inhibit the β-glucuronidase reaction was demonstrated in separate experiments.

HTS Activity Assay For UGT2B7. To overcome the limitations of existing UGT assay methods, an assay that measures UDP, which is produced via lysis of UDP-glucuronic acid in stoichiometric amounts with the glucuronidated products according to the following reaction is provided.

UDP-glucuronic acid+aglycone→UDP+glucuronide    Equation 1:

Unique advantages of UGT assays based on UDP detection include: a) reliance on the detection of a single product regardless of the UGT isozyme or the aglycone substrate being tested, thus greatly simplifying incorporation into an HTS format, b) direct quantification of reaction rate, thus allowing measurement of the kinetic parameters required for a mechanistic QSAR approach and providing a distinct advantage over assay methods based on competitive inhibition (such as the β-glucuronidase linked method described above), c) ability to use any of several absorbance based methods to detect nucleotides and allow signal detection in a multiwell format with no post reaction separation steps.

A UGT source for the HTS assays has been selected for both economic and technical reasons. Purified enzyme is required to eliminate interference by extrinsic factors with the QSAR analysis, and a recombinant source is required to provide a consistent source of highly enriched enzyme. While both transfected mammalian cells and BaV-infected inset cells have been used successfully for expression of UGTs, the BaV system offers greater economy and efficiency through lower media costs and easier scale up. The expession levels for UGTs in BaV-infected insect cells generally exceed those in transfected mammalian cells, and the enzymes retain their native kinetic properties. Methods for purification and lipid stabilization have been developed previously for isolation of the enzymes from native sources and are applied to BaV-expressed UGT2B7. Dr. Tephly's determinations of kinetic parameters for glucuronidation of opioids, steroids, and other compounds using mammalian cell membranes (Table I) will serve as a benchmark for evaluating the substrate specificity and catalytic efficiency of BaV-expressed UGT2B7 during expression and purification.

Purification and characterization of human UGT2B7 from baculovirus-infected insect cells. The cDNA for UGT2B7 has been subcloned into the BaV transfer vector pBlueBac (Invitrogen, San Diego, Calif.) and cotransfected with baculovirus DNA into Sf-9cells. Recombinant plaques were isolated and used to propagate high titer stocks of recombinant virus. The expression methods that are employed are similar to those used successfully for other UGT isozymes, including 1A 1, 1A6, 1A7, and 1A10. Parameters to be optimized for expression of UGT2B7 are media conditions, multiplicity of infection (MOI), cell type, and harvest time post infection. The initial approach, at the 100 ml scale, is to infect a serum free-adapted Sf-9 cell line at a high MOI (5–10) in Sf-900-II media (Gibco/BRL, Bethesda, Md.), and monitor expression over a period of five days post infection. After samples are removed, microsomal membrane fractions are prepared (100,00xg pellet) and assayed for the presence of UGT2B7 using androsterone glucuronidation activity (described below), Western blots, and SDS-PAGE. If low levels of expression are obtained in the initial experiments, the effect of media additives such as fetal calf serum and the use of different host cells (T. ni.) are tested. If these efforts yield reasonable expression levels (>1,000 pmol/min/mg), additional small scale runs will be performed to reduce the MOI and thus preserve the virus stock. The optimized shake flask methods then will be scaled up to 10–20 liter stirred bioreactors (B. Braun Biotech, Allentown, Pa.). Generally, this process is straightforward since oxygen availability and shear stress are fairly constant over this range with the culture methods used.

Micrsomal membranes from large scale batches (10–20 liters) of UGT2B7 expressing insect cells will be prepared and tested for activity and native substrate specificity. Some investigators have reported activation of "latent" UGT activity by addition of detergents, consistent with their location in the lumen of the endoplasmic reticulum. In general, we have not found that adding detergents such as CHAPS significantly increases UGT activity with the BaV expressed enzymes. Nonetheless, the effect of detergents on UGT2B7 activity will be tested during the course of expression optimization.

Following expression optimization, large scale (20–40 liters) batches of BaV infected insect cells will be grown and used as a source for the purified enzyme. Although the UGTs present some purification challenges due to their association with the membrane of the endoplasmic reticulum, methods for detergent solubilization and chromatographic separation have been developed for a number of rat, rabbit and human UGT isozymes isolated from liver tissue.

Briefly, cells will be lysed by extrusion using a Manton Gaulin Press. The microsomal fraction will be isolated by centrifugation and the membrane bound enzymes solubilized by detergent treatment. Although most UGT purifications described in the literature report the use of Emulgen 911 for solubilization, we also will test Triton N-101 due to its lower expense, greater availability in a more highly purified form, and our successful use in replacing Emulgen 911 for all of the P450 isozymes so far tested. The detergent-solubllized UGT will be purified using an empirically optimized combination of column chromatography steps. Those to be assessed include affinity chromatography (UDP-hexanolamine-Sepharose and omega-(beta-carboxyprionyl-amino)octyl-Sepharose), anion and cation exchange, hydroxylapatite, and chromatofocusing. Most of these resins have been used to purify various UGT isozymes from native sources.

The enzyme activity will be monitored during the course of the purification using the standard radioassay for androsterone glucuronidation. Purity will be assessed using SDS-PAGE. As with the P450s, the addition of lipid—most frequently phosphatidylcholine—is required to restore activity and maintain stability of purified UGTs. Optimal lipid composition and concentration for each of these purposes will be determined empirically for UGT2B7. Two-dimensional gel electrophoresis also will be used to determine whether multiple glycosylated forms of the UGT are being produced in insect cells. Some UGTs from native sources have been shown to be glycosylated, though no functional significance has been identified for this modification. Nevertheless, elimination of any type of structural heterogeneity is desirable for the intended QSAR analysis. Moreover, we have found that post-translational modifications sometimes can be optimized empirically by altering insect cell culture conditions.

A panel of aglycone substrates consisting primarily of opioids and steroids similar to those shown in Table I will be used to assess the substrate specificity of the BaV expressed, purified UGT2B7. Glucuronidation activity will be measured using standard methodology: quantification of radioactive glucuronide produced in reactions containing UDP-[$^{14}$C]-GlcA. Briefly, 100 µl incubations containing aglycone (100 µM–5 mM), purified UGT2B7, 100 mM Tris-HCl, pH 7.5, 10 mM MgCl$_2$, 10 mM saccharolactone, 0.1 mg/ml phosphatidylcholine, and 80 µM UDP-[$^{14}$C]-GA will be incubated at 37° C. for an appropriate period (0.5–2 hours depending upon the substrate). Different post reaction separation methods will be used depending upon the aglycone used. For opioids, the reactions will be quenched with 100 µl pre-chilled ethanol and vortexed. Precipitated protein will be removed by centrifugation. TLC will be used to resolve the glucuronidated products as described, which then will be quantified by scintillation counting following visualization by autoradiography. Reactions containing steroid substrates will be quenched with 100 µl of 0.7 M glycine-HCl/1% (v/v) Triton X-100, and the glucuronide product will be extracted with water-saturated ethyl acetate. After vortexing and centrifugation, 200 µl of the organic (upper) phase will be transferred to scintillation cocktail, and radioactivity determined by scintillation counting.

The specificity of the purified UGT2B7 will be assessed by determining overall catalytic efficiency with each aglycone substrate, as reflected in a ratio of the two fundamental Michaelis kinetic parameters, $V_{max}/K_m$. Reaction rates will be determined over a range of substrate concentrations and nonlinear regression will be used to fit the UGT rate data to velocity versus substrate curves (Graph Pad, Prism). $V_{max}/K_m$ values will be determined and compared with those determined with the enzyme isolated from HK293 cells (Table 1). In addition, the ability of UGT2B7 to glucuronidate morphine at both the 3-OH and 6-OH will be used to assess whether the purified enzyme retains native regioselectivity. In both human liver microsomes and HK293 microsomes expressing UGT2B7, the ratio of proximately 7:1 is observed for the $V_{max}$ for the formation of morphine-3-glucuronide vs. morphine-6-glucuronide. This ratio will be determined for the purified enzyme using HPLC-based methods for separation and quantification of the two glucuronides.

To ensure that the proposed HTS assays fully address the UGT QSAR study requirements and current market needs, the following feasibility goals must be met for production of the purified protein:

Production of 20 mg batches of UGT2B7 with 90% purity as assessed by Coomassie-blue stained SDS-PAGE.

Adequate stability (maintenance of 80% of activity) at room temperature for 2 hrs after a single freeze-thaw.

Substrate specificity similar to the enzyme expressed in HK293 cells as assessed by rank ordering of test substrates based on $V_{max}/K_m$ values (Table I).

Development of an HTS UGT activity assay based on UDP detection. The basis of the proposed UGT assay is measurement of UDP formation indirectly by coupling to the apyrase catalyzed production of inorganic phosphate. Phosphate will be detected colorimetrically at concentrations as low as 100 nM (10 pmol) in microtitre plates (100 µl volume) following formation of a complex with molybdate and malachite green. This will be sufficiently sensitive for initial velocity kinetics with the UGTs because very few known aglycone substrates have $K_m$ values lower than 10 µM. Thus, detectable levels of product can be formed from subsaturating concentrations of substrate without depleting the pool of substrate to a level that would significantly affect reaction rate.

TABLE 3

Apyrase coupled assay for the colorimetric measurement of UGT activity.

1. UGT reaction: UDPGA + Aglycone → Glucuronide + UDP
2. Apyrase reaction: UDP → UMP + P$_i$
3. Colorimetric reaction: Pi + molybdenum/malachite green → A$_{630}$ @ 1 mM = 100

The protocol for the phosphate-linked assay method is as follows: 1) UGT reaction components, including purified UGT2B7, lipids, buffer, effectors, and UDPGA and apyrase will be precombined and dispensed into microtitre plates; 2) the reactions will be initiated by the addition of aglycone substrates from concentrated stock solutions in DMSO and incubated at predetermined temperatures and time periods; 3) the reactions will be quenched by the addition of the highly acidic molybdate/malachite green color reagent; 4) after a suitable time period (10–30 minutes) for color development, absorbance will be determined using a multiwell plate reader. Standard curves for phosphate are determined and used to convert the absorbance values to nanomoles of glucuronide produced assuming a 1:1 stoichiometry with UDP formation (Equation 1). The simplicity of this method makes it highly useful for the HTS approaches required to adequately survey the structural diversity of UGT substrates.

UGT reactions are optimized for enzyme amount, buffer and metal composition, lipid composition and concentration, and UDPGA concentration. Apyrase reactions are optimized primarily for the amount of enzyme required to rapidly hydrolyze the minimum amounts of UDP expected in the assay (approx 10 pmol), and tested for inhibition by a number of aglycones from various structural classes. The colorimetric phoshate detection method is optimized primarily for composition of the color reagent (acidity, amounts of molybdenum and malachite green, addition of detergent or organic solvents to increase solubility malachite green) and tested for interference from UGT reaction components and aglycones.

For the QSAR studies, the assay is capable of quantitatively measuring UGT turnover of strucurally diverse aglycones, including both very good and very poor substrates.

The assay has sufficient sensitivity for kinetic analysis with substrates that are glucuronidated very slowly (low $V_{max}$) or at low concentrations (low $K_m$). The assay is used for qualitative screening of compounds to detect glucuronidation, and for detailed kinetic analyses of those aglycones identified as substrates. Since an excess of enzyme can be used, it should be possible to detect even very poor UGT substrates in the screening mode. Based on the activities obtained with crude cell fractions, and the turnovers for other purified UGTs, purified UGT2B7 is expected to have a $V_{max}$ of at least 100 nmol/min/mg with good substrates such as morphine. Thus, using 1 μg of UGT2B7 per assay, and assuming subsaturating substrate concentration and a low $V_{max}$ such that the enzyme is operating at a rate of only 1.0 nmol/min/mg, the amount of product generated in 100 minutes is 100 pmol, ten-fold higher than the detection limit of the assay.

However, there are some special considerations that must be addressed to use the assay in the analytical mode at very low substrate concentrations. As a practical guideline for initial velocity kinetics, it is undesirable to consume more than 10% of the aglycone substrate during the course of the reaction. At the same time, sufficient product is needed to allow detection using the apyrase coupled reaction. Determination of UGT kinetic parameters will involve aglycone concentrations as low as 1 μM. Consumption of 10% of the aglycone substrate present at a starting concentration of 1 μM in a 100 μl volume would produce 10 pmol of product, which is exactly at the estimated lower limit of detection for the assay. Because purified components are used in these studies, it may be possible to adjust enzyme concentrations and incubation times to allow accurate measurement of these low levels of product formation. If not, it may be necessary to increase the reaction volumes and enzyme amounts several-fold at the low substrate concentrations (thereby increasing product formation by the same factor) and then concentrate the reactions prior to colorimetric detection.

Given the proportionately small number of reactions that are run at the lower substrate concentrations, this should be feasible; very few known UGT2B7 substrates have $K_m$ values less than 20 μM (Table I). The NAD-linked assay method described below provides another alternative for increasing the sensitivity.

Rapid and complete conversion of UDP to UMP and $P_i$ by apyrase. Apyrase is a commercially available enzyme that specifically cleaves the terminal phosphate from nucleotide di- and triphosphates, including UDP (Sigma, St Louis, Mo., 55–57) (the UGT donor molecule UDPGA is not a substrate for apyrase). Because cleavage of the UDP phosphodiester bond is highly favored thermodynamically, the reaction will go essentially to completion. However if the levels of UDP are significantly lower than the $K_m$ for apyrase, the rate of hydrolysis is slower. Based on a $V_{max}$ of 50 1 μmol/min/mg—approximately 500-fold faster than the estimated $V_{max}$ for purified UGTs—and assuming that the $K_m$ for UDP is within an order of magnitude of that for ADP (100nM), a relatively small amount of apyrase should rapidly hydrolyze UDP amounts at the lower end of the detection limit for phosphate (100 nM). TLC based assays with [$\beta$-$^{32}$P]UDP (produced enzymatically from [$\gamma$-$^{32}$P]ATP and UMP) are used to determine the extent of UDP hydrolysis at low UDP concentrations and to monitor the reaction if optimization is required. If apyrase proves unsuitable for any reason, a number of pyrimidine nucleotidases that have been purified and characterized may prove useful. Some of these will remove both phosphates from UDP, thus increasing the sensitivity of the assay method twofold.

Tight coupling between UDPGA hydrolysis and production of glucuronides; i.e., lack of significant glucuronidase activity by UGTs or contaminating proteins. Based on prior studies, there should be very little nonproductive UDPGA hydrolysis catalysed by the purified UGT2B7 or by other purified UGTs that will eventually be incorporated into this assay format. In one report, the alpha glucuronidase activity of a purified porcine UGT was approximately 1% of the rate of aglycone glucuronidation, and increased to approximately 4% in the presence of some inhibitors believed to bind at the aglycone site. These results and the prior demonstration that UGT activity can be measured accurately by coupling to UDP dependent NADH oxidation suggest that nonproductive UDPGA hydrolysis will not contribute significantly to background noise in the assay. Independent measurements of glucuronide formation by standard methods (isolation of radiolabelled glucuronides formed from $^{14}$C-UDPGA) in parallel with the phosphate detection method are used to test for this possibility. If necessary, adjustments to the UGT reaction conditions such as changes in lipid composition or metals are made to minimize non-productive UDPGA hydrolysis.

Background phosphate from sources such as hydrolysis of UMP or from phospholipids used for reconstitution of UGTs minimized. Although the use of purified UGT2B7 should greatly decrease the level of background phosphate present in the UGT reactions, some potential remains for phosphate to be released nonspecifically from lipids or nucleotides. For example, after addition of the color reagent to the UGT reaction, the final assay mix will be approximately 0.2N $H_2SO_4$, which may be sufficiently acidic to cause acid hydrolysis of phosphoester bonds in UMP, UDPGA, and phospholipids (required for UGT activity). This would increase the background absorbance of the assay. If this occurs, conditions other than acid pH that can be used to maintain the solubility of the malachite green will be investigated, such as addition of organic solvents or detergents. Alternatively, it may be possible to neutralize the reactions after color development is complete (approximately 10 minutes) to minimize acid hydrolysis of phosphoesters.

NMR will be the main approach used for the structural studies because it will provide dynamic 3-D structures both for bound aglycones and for the UGT aglycone binding domain. Though X-ray crystallography can generate higher resolution structures, it only captures a single conformation of a protein/ligand complex, which may not reflect the biologically relevant structure. In addition, it is higher risk and more time consuming than NMR, and thus not practical for obtaining multiple structures within the time period of the study. The NMR studies will require a soluble, properly folded UGT2B7 fragment that retains the aglycone binding properties of the full length protein and that meets the size requirements for the different types of NMR studies that will be performed. For NMR analysis of bound ligands using transferred nuclear Overhauser effects, the optimal polypeptide size range is 30–70 kDa, whereas solution structures for proteins are very difficult to obtain above 25 kDa. The rationale for determining the specific N-terminal fragment of UGT2B7 to be produced for aglycone binding studies is based on a combination of empirical studies on other UGTs and modeling studies based on the known structure of other opioid binding proteins, as described below.

Multiple lines of evidence, including functional expression of chimeric UGTs in which the N- and C-terminal halves of different isozymes were exchanged, suggest that the aglycone binding site is in the amino terminal half of the protein. Based on these observations, it has been has proposed that the region between amino acids 60 and 120 likely represents part of the aglycone binding site. In addition, extensive conformational searches have been performed using the Sybyl Biopolymer program (Tripos, St. Louis, Mo.) based on homology comparisons with other UGTs that recognize opioids and known structural features for other opioid binding proteins, including CYP2D6 and the $\mu$-opioid receptor. The resulting structural model suggests that the pocket formed by Lys95, Arg96, and Asp99 in UGT2B7 is part of the aglycone binding site.

Accordingly, an 18.2 kDa fragment of UGT2B7 including amino acids 24–180 with a cleavable 14 kDa affinity tag as an N-terminal translational fusion will be produced for the structural studies. Use of this construct will allow production of a 32 kDa fusion for NMR ligand binding studies and its proteolytic cleavage in vitro will produce the 18.2 kDa UGT2B7 domain, a suitable size for determination of an NMR solution structure. Amino acids 1–23 of UGT2B7 will not be included in the construct as this is the signal peptide removed by posttranslational processing in mammalian cells. The construct will be terminated at a possible SV8 protease site at amino acid 180 because protein structure studies indicate that functional subdomains often are bound by protease sites. The IgG binding domain of Protein A will be used as an N-terminal affinity tag as it has been shown to allow proper folding of fusion partners. A similar fusion was used for the expression of subdomains of UGT2B4, including amino acids 14–150, that bound UDPGA.

Production and characterization of a soluble aglycone binding domain of UGT2B7. Using PCR, the 24–180 amino acid domain from the UGT2B7 will be amplified in the pBluescript vector (Stratagene) using oligonucleotide primers with suitable restriction sites (e.g.EcoRI and XbaI) and a stop codon. The product will be ligated into the expression vector pEZZ18 (Amersham-Pharmacia), which contains the protein A signal sequence and two synthetic Z domains based on the IgG binding domain of protein A and the resulting vector pEZZ182B7 will be transformed into E.coli HB101. The entire insert and flanking sequences will be sequenced to confirm that no mutations were introduced.

Because of the protein A signal sequence, the fusion protein, ZZ-2B7(24–180) should be largely secreted into the medium, thereby avoiding inclusion body formation and the need for refolding. Increased secretion of ZZ fusion proteins is observed in aerated fermentors relative to shake flask culture methods, therefore the bacteria will be grown in 10 liter controlled fermentors. The fusion protein will be purified from the media using an IgG-Sepharose 6 column (Amersham-Pharmacia). Additional chromatography on ion exchange or other resins will be employed if needed to achieve purity of greater than 95% as assessed by SDS-PAGE. It is possible to obtain up to 100 mg/liter protein using the pEZZ18 vector and a fermnenter. Use of this expression system will enable production of the large quantity of proteins required for the subsequent structural studies. Other commercially available fusion protein expression systems such as the glutathione transferase based system (Pharmacia) will be assessed if the pEZZ18 vector system proves unsuitable.

The secondary structure of the UGT2B7 fusion protein will be examined using circular dichroism spectroscopy to assess the extent of ordered folding versus misfolded protein. This Method also may be used in combination with aglycone binding studies to aid in determining optimal buffer and additives required to maintain native conformation.

Binding constants will be determined using a two step process in which the ligand exchange regime is characterized first, then the equilibrium and rate constants for ligand dissociation ($K_d$ and $K_i$) are found using a method suited for the estimated exchange rates. Effort will be concentrated on the aglycone spectra, as the UGT2B7 fusion protein is large enough so that its spectra will probably not be useful in elucidating exchange data. In the characterization step, spectra will be taken of solutions containing the pure aglydone, a series of solutions with ratios of aglycone to protein from 0.1 to 5, and a sample of pure protein. The spectra will then be analyzed for evidence of the exchange regime. Concentrations and temperature will be varied until a clear fast or slow exchange regime is reached. With knowledge of the exchange regime and the resulting estimates of binding parameters, the binding constants can then be accurately determined. The concentration dependence of lineshape and line shift changes will be used to determine the binding constants for systems in fast exchange. Slowly exchanging systems will be studied by magnetization transfer techniques. Simple, slowly exchanging aglycones will be studied by saturation transfer experiments.

The foregoing is considered as illustrative only of the principles of the invention. Further, since numerous modifications and changes will readily occur to those skilled in the art, it is not desired to limit the invention to the exact construction and operation shown and described. Therefore, all suitable modifications and equivalents fall within the scope of the invention.

We claim:

1. A method of quantifying the amount of uridine diphosphate (UDP) in a sample comprising the steps of:
   a. incubating said sample with an enzyme capable of cleaving a phosphate group from said UDP under conditions that would allow said enzyme to be active;
   b. quenching said phosphate cleavage reaction;
   c. adding to said sample molybdenum/malachite green and incubating for a period of time sufficient for color development; and
   d. spectrophotometrically analyzing said sample.

2. The method according to claim 1, wherein said enzyme capable of cleaving a phosphate group from UDP is selected from apyrase or a pyrimidine nucleotidase.

3. The method according to claim 1, wherein, prior to step a, said UDP is generated by the action of an UDP-glucoronosyltransferase on an aglycone in the presence of uridine 5'-diphosphoglucuronic acid.

4. The method according to claim 1, wherein steps a, b and c are performed in a single vessel.

5. The method according to claim 3, wherein said generation of UDP, step a, step b and step c are performed in a single vessel.

6. A method of determining if a compound is a substrate for an UDP-glucoronosyltransferase comprising the steps of:
   a. providing a solution comprising a UDP-glucoronosyltransferase, uridine 5'-diphosphoglucuronic acid and an enzyme capable of removing a phosphate group from UDP, wherein said solution provides conditions that allow said UDP-glucoronosyltransferase and said enzyme to be active;
   b. adding said compound to said solution;
   c. quenching said phosphate cleavage reaction;
   d. adding to said sample molybdenum/malachite green and incubating for a period of time sufficient for color development; and
   e. spectrophotometrically analyzing said sample.

7. The method according to claim 6, wherein said enzyme capable of cleaving a phosphate group from UDP is selected from apyrase or a pyrimidine nucleotidase.

8. The method according to claim 6, wherein said method is adapted for high throughput screening.

* * * * *

UNITED STATES PATENT AND TRADEMARK OFFICE
CERTIFICATE OF CORRECTION

PATENT NO. : 6,551,790 B2
DATED : April 22, 2003
INVENTOR(S) : Olga V. Trubetskoy and Robert G. Lowery It is certified that error appears in the above-identified patent and that said Letters Patent is hereby corrected as shown below:

<u>Title page,</u>
Item [56], References Cited, OTHER PUBLICATIONS, please insert:

-- G.J. Mulder and A.B.D. Van Doorn, "A Rapid $NAD^+$-Linked Assay for Microsomal Uridine Diphosphate Glucornyltransferase of Rat Liver and Some Observations on Substrate Specificity of the Enzyme," <u>Biochem. J.</u>, 1975, 151:131-140

A. Colin-Nieger et al., "Assessment of the Mulder and Van Doorn Kinetic Procedure and Rapid Centrifugal Analysis of UDP-Glucoronosyltransferase Activities," <u>J. Biochem. Biophys. Meth.</u>, 1984, 9:69-79 --

Signed and Sealed this

Eighth Day of June, 2004

JON W. DUDAS
*Acting Director of the United States Patent and Trademark Office*